United States Patent
Maev et al.

(10) Patent No.: US 9,613,401 B2
(45) Date of Patent: Apr. 4, 2017

(54) METHOD TO OBTAIN 3D IMAGES OF A FLOWING REGION BENEATH AN OBJECT USING SPECKLE REFLECTIONS

(71) Applicant: Tessonics Corp., Birmingham, MI (US)

(72) Inventors: Roman Gr. Maev, Windsor (CA); Jeffrey T. Sadler, Chatham (CA); Eugene Malyarenko, Troy, MI (US)

(73) Assignee: TESSONICS CORPORATION, Birmingham, MI (US)

( * ) Notice: Subject to any disclaimer, the term of this patent is extended or adjusted under 35 U.S.C. 154(b) by 327 days.

(21) Appl. No.: 13/863,357

(22) Filed: Apr. 15, 2013

(65) Prior Publication Data

US 2013/0272597 A1  Oct. 17, 2013

Related U.S. Application Data

(60) Provisional application No. 61/623,847, filed on Apr. 13, 2012.

(51) Int. Cl.

| G06K 9/00 | (2006.01) |
|---|---|
| G06T 5/00 | (2006.01) |
| A61B 8/06 | (2006.01) |
| G01S 15/89 | (2006.01) |
| G01S 7/52 | (2006.01) |
| A61B 8/08 | (2006.01) |
| G01F 1/66 | (2006.01) |

(52) U.S. Cl.
CPC ......... *G06T 5/002* (2013.01); *A61B 8/06* (2013.01); *A61B 8/483* (2013.01); *A61B 8/5223* (2013.01); *G01S 7/52026* (2013.01); *G01S 15/8981* (2013.01); *G01F 1/66* (2013.01); *G01S 15/8993* (2013.01)

(58) Field of Classification Search
CPC  G06T 5/002; A61B 8/06; A61B 8/483; A61B 8/5223; G01F 1/66; G01S 15/8981; G01S 15/8993; G01S 7/52026
See application file for complete search history.

(56) References Cited

U.S. PATENT DOCUMENTS

| 5,632,277 A | 5/1997 | Chapman et al. |
|---|---|---|
| 5,980,459 A | 11/1999 | Chiao et al. |
| 6,155,981 A | 12/2000 | Ermert et al. |
| 6,186,949 B1 | 2/2001 | Hatfield et al. |

(Continued)

FOREIGN PATENT DOCUMENTS

EP  1 122 556 A2  8/2001

OTHER PUBLICATIONS

International Preliminary Report on Patentability for PCT Application No. PCT/US2013/03667, mailed Oct. 23, 2014.

(Continued)

*Primary Examiner* — Tom Y Lu
(74) *Attorney, Agent, or Firm* — Carlson, Gaskey & Olds, P.C.

(57) ABSTRACT

A method for imaging a flowing media within static regions includes obtaining a plurality of signals using the speckle properties of the flowing media. The plurality of signals are compared to one another such as by subtraction. The static regions are removed from the plurality of signals by the comparison. The remaining signals are combined (such as by summing) to produce an image of the flowing media.

29 Claims, 5 Drawing Sheets

(56) References Cited

U.S. PATENT DOCUMENTS

| | | | |
|---|---|---|---|
| 6,210,332 | B1 | 4/2001 | Chiao et al. |
| 6,547,731 | B1* | 4/2003 | Coleman ................. A61B 8/06 600/455 |
| 7,803,116 | B2 | 9/2010 | Sikdar et al. |
| 2008/0269611 | A1* | 10/2008 | Pedrizzetti et al. .......... 600/454 |
| 2009/0018449 | A1* | 1/2009 | Raju ............................ 600/455 |
| 2009/0043208 | A1* | 2/2009 | Hergum et al. ............... 600/455 |
| 2012/0063665 | A1* | 3/2012 | Wang ................... A61B 5/0066 382/134 |
| 2012/0143058 | A1* | 6/2012 | Powers ............... G01S 7/52077 600/443 |

OTHER PUBLICATIONS

International Search Report for PCT Application No. PCT/US2013/036667, Jun. 19, 2013.

Bohs et al., "Ensemble Tracking for 2D Vector Velocity Measurement: Experimental and Initial Clinical Results," IEEE Transactions on Ultrasonics, Ferroelectrics and Frequency Control, IEEE, US, vol. 45, No. 4, Jul. 1, 1998, pp. 912-924, XP011434732.

Vray et al., "High Frequency B-mode Ultrasound Blood Flow Estimation in the Microvasculature," 2004 IEEE Ultrasonics Symposium, Montreal, Canada, vol. 1, Aug. 23, 2004, pp. 466-469, XP010783984.

Ishihara et al., "High-Speed Digital Subtraction Echography: Principle and Preliminary Application to Arteriosclerosis, Arrythmia and Blood Flow Visualization," Proceedings of the Ultrasonics Symposium, Honolulu, vol. 3, Dec. 4, 1990, pp. 1473-1476, XP000289856.

\* cited by examiner

2D VERTICAL CROSS SECTION

FIG.3

2D VERTICAL CROSS SECTION

METHOD TO OBTAIN 3D IMAGES OF A FLOWING REGION BENEATH AN OBJECT USING SPECKLE REFLECTIONS

BACKGROUND

This invention relates generally to the medical imaging field, and more specifically to a method and system using ultrasound for imaging of blood flow, or other dynamic systems (tissue motion) through the human skull bone, or through other tissues (muscle, fat, etc.) in the medical imaging field.

All existing ultrasonic blood flow imaging algorithms exploit the phenomenon of ultrasonic reflection from the moving speckles in the blood (e.g. erythrocytes, air bubbles etc). Doppler methods are most effective when ultrasonic waves propagate parallel to the blood flow. Speckle tracking, speckle interferometry, and B-Flow methods are direction-insensitive. All listed methods are capable of overcoming the most common imaging obstacles, such as relatively weak useful echoes compared to the blood vessel wall reflections, and attenuation of acoustic waves by soft tissues. Imaging through the skull, however, is a more serious problem, and here all listed methods have their respective shortcomings.

Transcranial ultrasonic imaging of the blood flow is hampered by scattering, attenuation, and multiple reflections of acoustic waves at the surface and inside the skull. These effects tend to attenuate and distort the ultrasonic field transmitted through the skull, causing image quality degradation and resolution loss. Human adult skull bone is inhomogeneous, comprising three principal layers. The outer and inner layers, which are present not only in adults but also in children and animals, are composed of compact bone. A middle porous layer that is only present in adult humans turns out to be the main contributing factor to distortion of transcranial ultrasonic waves. Existing attempts to grapple with these problems are either invasive or require high-power ultrasound, which could harm the brain tissue. At clinically acceptable power levels and at relatively low ultrasonic frequencies allowing skull penetration the speckle reflections and even blood vessel wall echoes are typically buried in the noise, so that the amplitude-based algorithms fail. One existing algorithm that could potentially handle this issue is depth-insensitive and would produce a 2D projection of all blood vessels on the imaging (array) plane.

Thus, there is a need in the medical diagnostics field to create an improved method and a practical system using ultrasound for full 3D imaging of blood flow, or other dynamic systems (tissue motion) through the human skull bone, or through other tissues (muscle, fat, etc.) in the medical imaging field. This invention provides such an improved method and system.

SUMMARY

Blood flow can generally be imaged by using the scattered information from the "speckles" or backscattered information created from flow of blood cells and platelets in the blood. Most techniques use these speckles, but only work in surface blood vessels due to heavy acoustic losses when ultrasound is transmitted through the skull, or used in deep tissue.

Medically a major (carotid) artery extends from the heart, through the neck and towards the brain. According to medical doctors this is where the majority of blockages that cause serious strokes occur as it directly feeds the brain its supply of blood. Visualizing blood flow of this can show the restricted area. Visualizing blood flow can also show narrowing, and restrictions of other areas. Visualizing blood flow can also show abnormalities like aneurysms. Also, certain types of tumors have high concentrations of blood vessels. Generally this method can be adapted to image any type of flow that has speckle properties, or where speckle properties can be introduced.

The present method is specifically designed to deal with loss of information due to skull of deep tissue and is specifically designed to remove other static objects. The present method is designed to do this by using a statistical, or multiple information approach. Multiple signals are obtained (and processed to enhance the signal). Each signal is compared mathematically to all other signals, this allows the process to turns N signals into roughly $N^2/2$ measurements. Multiple comparisons are then combined to help form the image Using this extra information, and comparing in a way to greatly inflate the value of the information (N Scans gives roughly $N^2/2$ data measurements) provides the extra information necessary to deal with losses from skull, and image the scatterers in the blood flow The present method is able to image regions of flow, distinguishing them from non-flowing regions (static regions are eliminated, and may be overlaid via other methods). The present method is able to image regions of flow beneath or through an object. The present method uses the speckle, or scattering, properties of the liquid, where the flowing material produces a scattered signal to be detected and analysed to create the image of the flowing region.

Scattering particles (contrast agents) may also be introduced to the liquid to enhance or produce speckle properties. Speckle properties of flowing region may be due to reflections from individual scatterers, or multiple scatterers acting as a group.

In a first example application, for imaging blood flow beneath the human skull, blood cells and platelets create the speckle scattering.

In a second example application, for imaging blood flow through human tissue, blood cells and platelets create the speckle scattering.

In a third example application, the present method can be used for imaging flow of a liquid through a pipe.

The present method images regions of blood flow and distinguishes them from non-flowing regions. The static regions are eliminated, and may be overlaid via other methods.

Speckle, or scattering, properties of blood (blood cells, platelets) and possible contrast agents are used. This speckle property produces a scatter signal to be detected and analyzed to create the image of the flowing region.

In particular, regions of blood flow beneath the skull (and through brain tissue) are of interest, but the present method is also applicable to regions of blow beneath tissue (muscles, fat). Additionally, traditional near-surface blood flow imaging is also possible (but is not the focus or advantage of the present method). The present method is also possibly applicable in other dynamic systems in the body (tissue motion).

There may also be extended application to non-medical dynamical systems, such as any system of "flow through a pipe," or possibly even "motion beneath a surface."

DETAILED DESCRIPTION OF A PREFERRED EMBODIMENT

Figure 1:
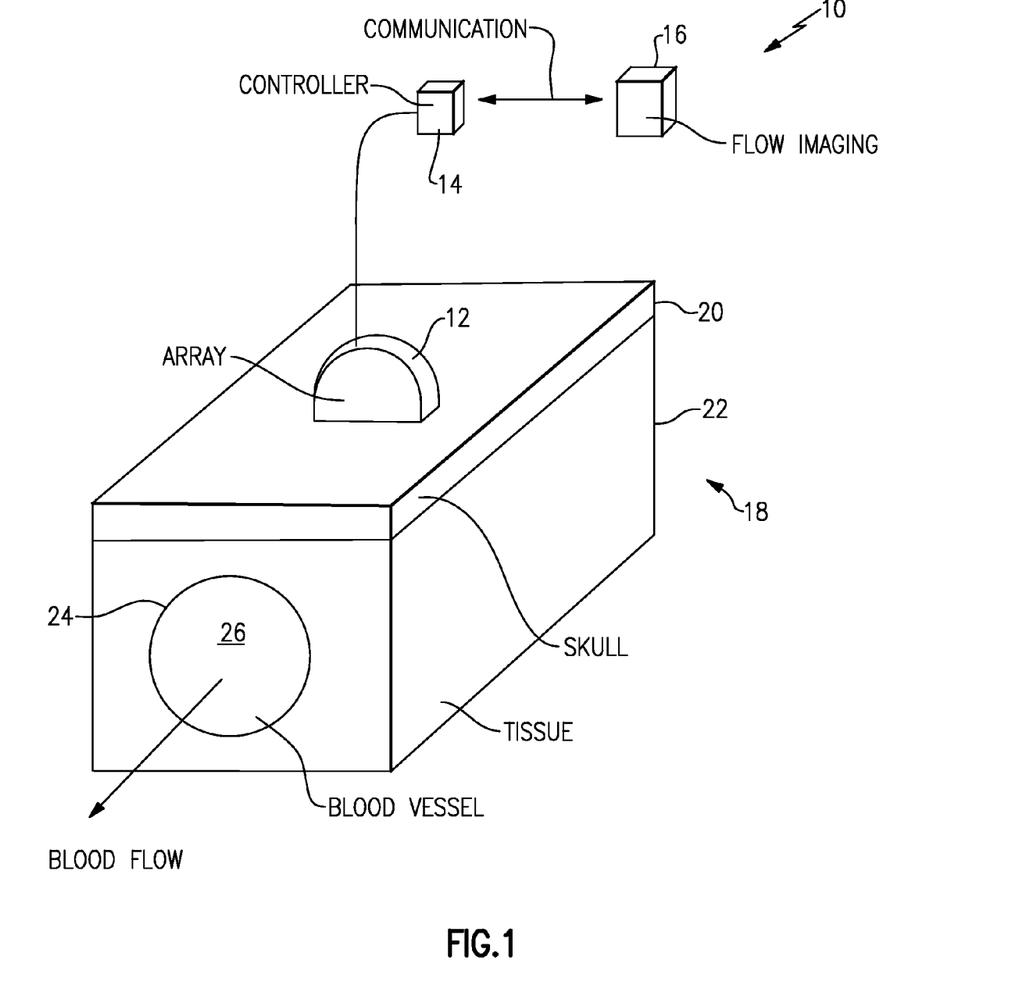
FIG. 1 schematically shows a flow imaging system monitoring blood flow in a head.
Figure 2:
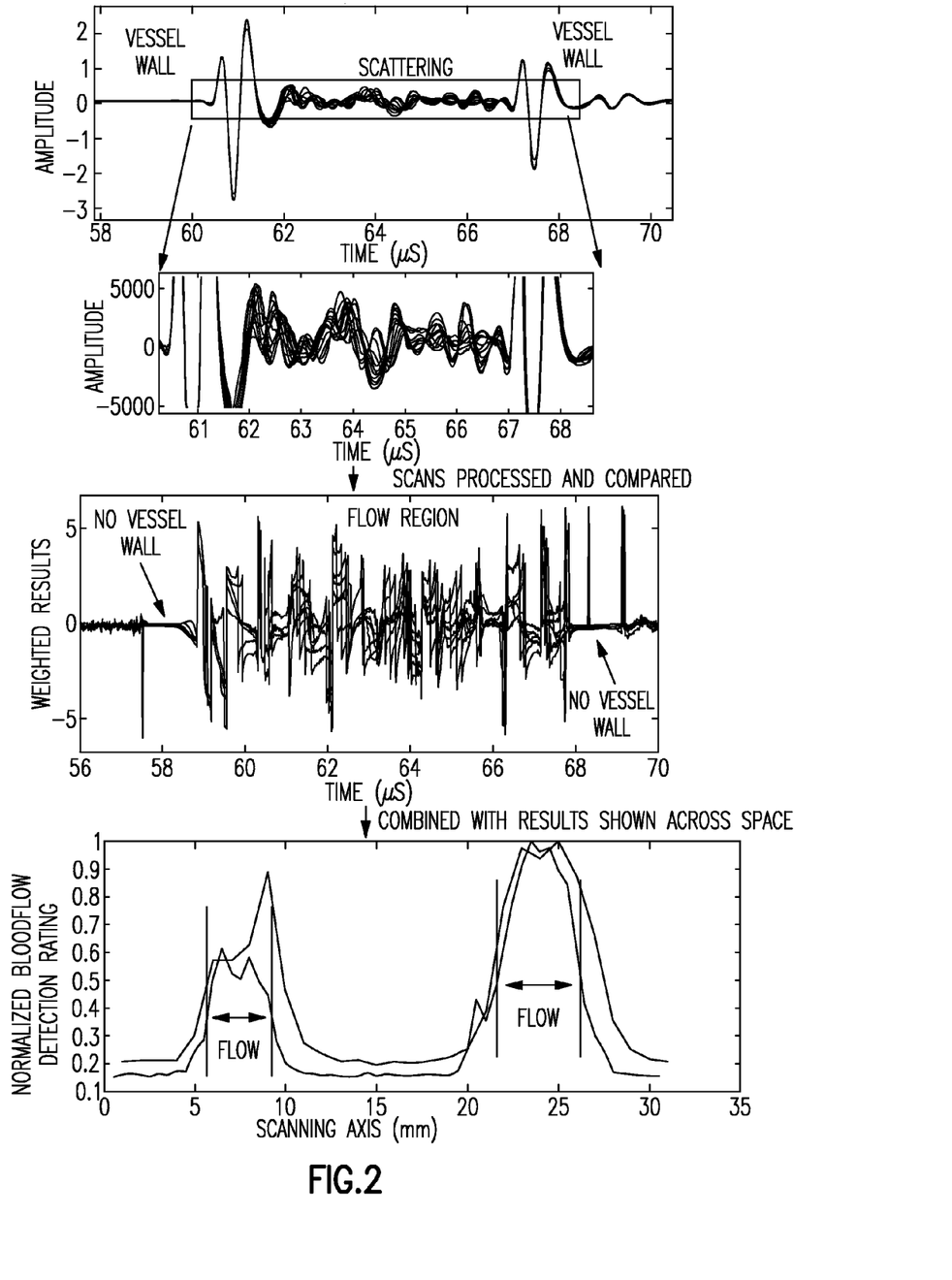
FIG. 2 shows one embodiment of the flow imaging technique, showing speckles being enhanced, then combined over the special domain to produce an image showing blood flow regions.
Figure 3:
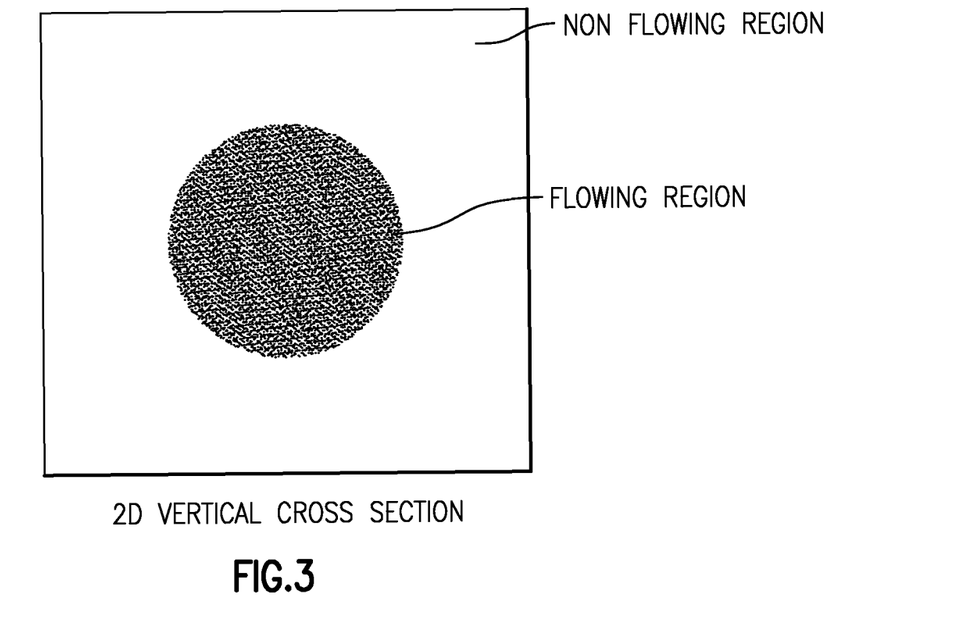
FIG. 3 is an example 2D cross section of a flow imaging output from the system of FIG. 1.
Figure 4:
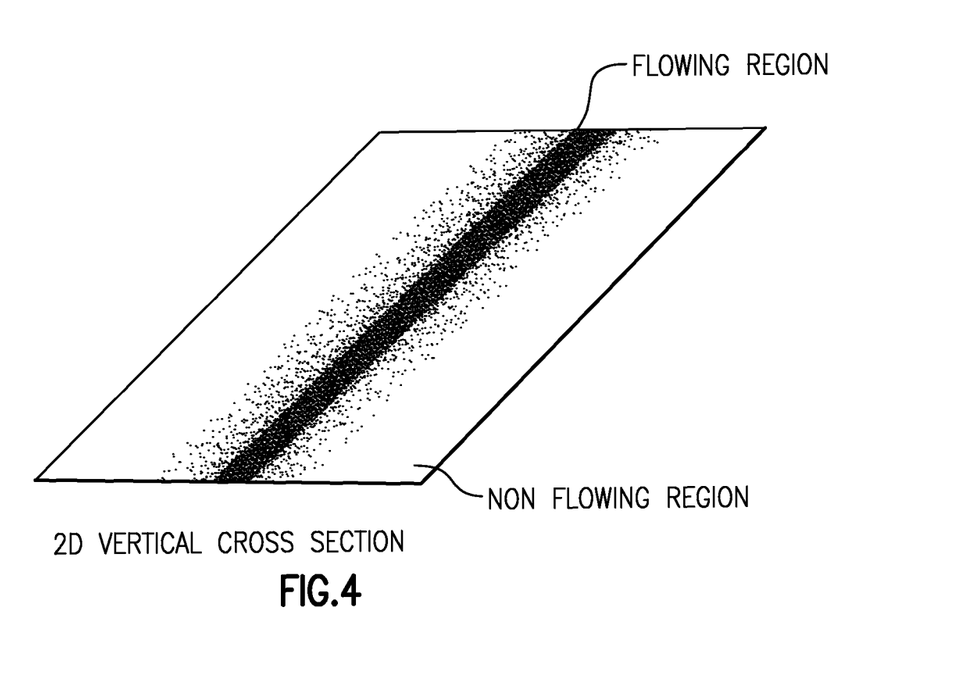
FIG. 4 is an example 2D cross section of a flow imaging output from the system of FIG. 1.
Figure 5:
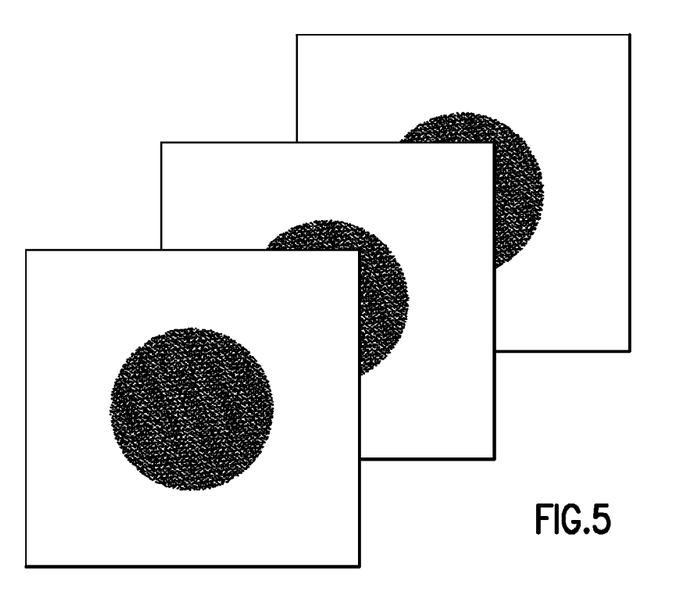
FIG. 5 shows multiple cross sections of a flow imaging output from the system of FIG. 1.
Figure 6:
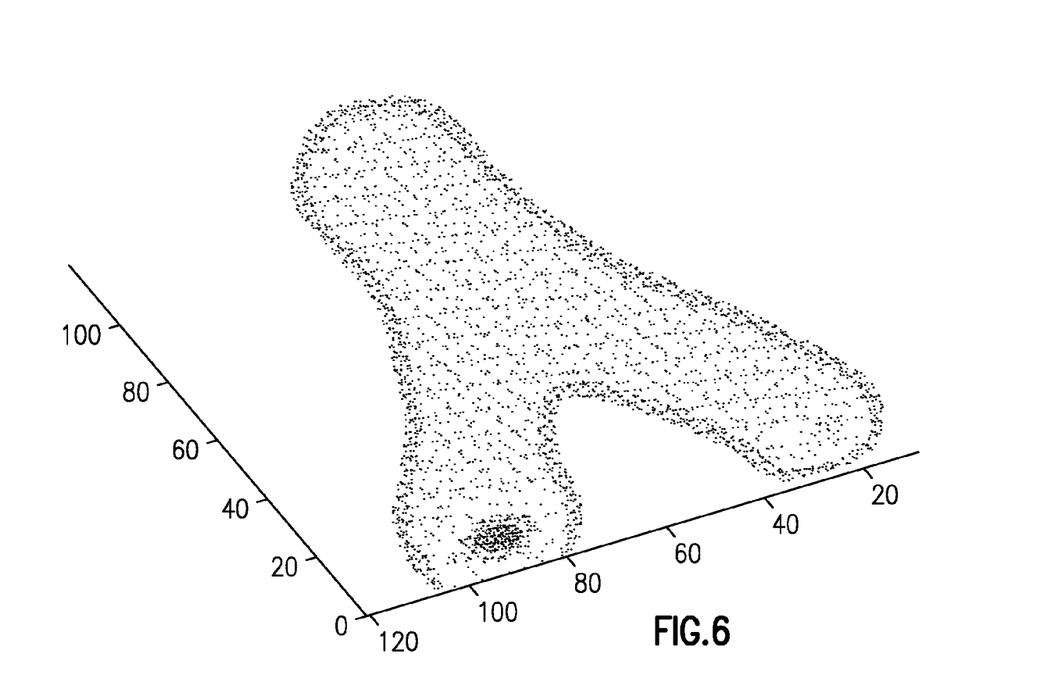
FIG. 6 shows an example 3D output of flow imaging system of FIG. 1.
Figure 7:
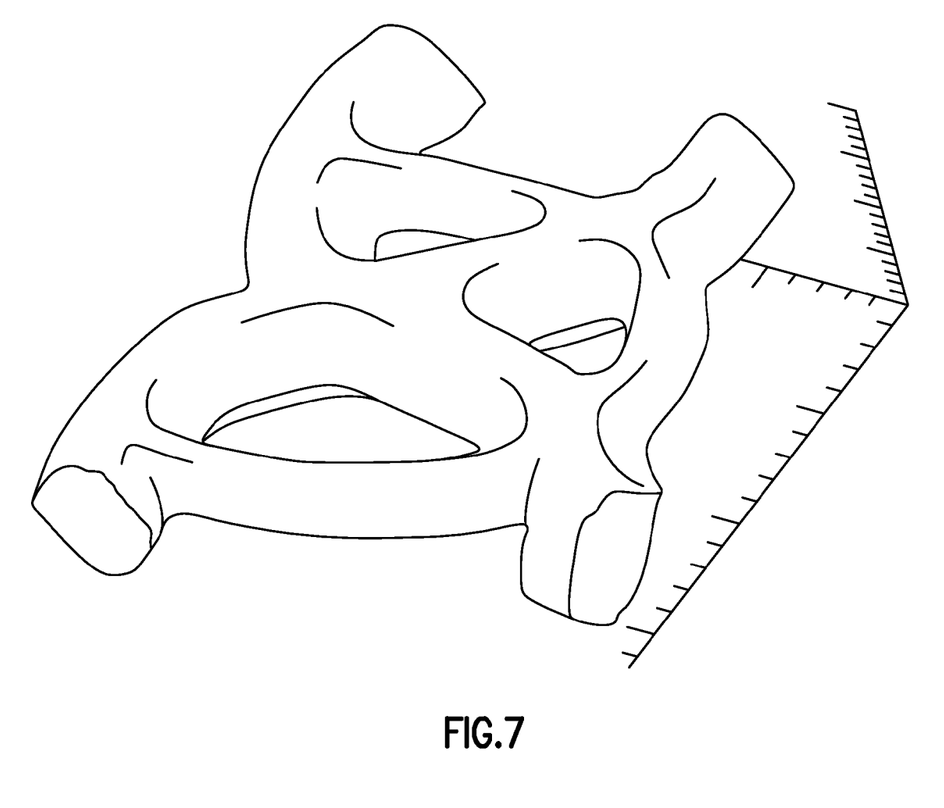
FIG. 7 shows an example 3D output of flow imaging system of FIG. 1.

A flow imaging system 10 according to one embodiment is shown schematically in FIG. 1. The system 10 includes an imaging device 12, a controller 14 and an image-processing computer 16. The system 10 can be used, for example, as shown in FIG. 1 on a human head 18. The head 18 includes a skull 20 outward of soft tissue 22. A blood vessel 24 is within the soft tissue 22 spaced away from the skull 20. Blood 26 flows through the blood vessel 24.

Generally, images from the imaging device 12 (optionally, as controlled by controller 14) are received and stored by the flow imaging computer 16. Generally, the algorithms described herein are performed by the flow imaging computer 16 on the images stored thereon, as received from the imaging device 12. The flow imaging computer 16 includes a processor, storage (such as memory, mass storage, hard drive, optical drives, or other magnetic, electronic or optical storage), optional graphics processor and user interfaces, such as a display.

Many alternatives for hardware are possible in implementing the method of the present invention. The present techniques discussed here are not restricted to any specific device, and can be implemented in a new device designed for this particular methodology, or an existing device modified to obtain the required signal or data.

1. Signal Acquisition

The imaging device 12 can be an existing device to obtain the required signals or data. This imaging device 12 (or system) is responsible for signal acquisition.

The scanning device 12 is any device capable of generating, receiving, and storing data created from radiation of the physical factor obtaining an A-Scan (temporal vs. Amplitude data, depth vs. Amplitude, temporal vs. intensity, etc depending on scanning system). This imaging device 12 is able to obtain this data over a 1D, or 2D area in space, in addition to A-Scan data above.

The imaging device 12 can be made up of separate transmitters (source) and receivers, or a single transmitter-receiver. The source, or transmitter, may be any of the following: a single element transmitter, a one-dimensional array, or two-dimensional array. This generates the field to create the radiation for the physical factor. The receiver is preferred to be a one dimensional or two-dimensional array. A motorized single element receiver is possible. This device receives the signal of the radiation from the physical factor.

These signals acquired by the imaging device 12 can be processed in parallel by the methodology, or signals obtained and then processed. It is possible to enhance the results of the methodology by a second data acquisition by the imaging device 12.

The imaging device 12 obtains data in the form of multiple A-Scans (amplitude vs. time), with each set of A-Scans being obtained at a specific spatial region.

Multiple sets of A-Scans can also be taken at different spatial regions form a 2D, or 3D image, this can be done by receiving data at different elements of the receiver, steering of the beam, or controlled physical motion of the receiver. The methodology depends on the scanning system in question.

2. Methodology & Data Processing

General Overview

The invention uses the set of A-Scans (from scanning system above) to create an image, or sub-set of a larger images indicating the region of blood flow This is done by comparing the information from the individual acoustic waveforms acquired during the measurement (or comparing processed waveforms). Two examples are provided below:

Comparing pairs of waveforms:

i.e. compare signal 1 with signal 2, signal 2 with 3, and so on for a set number of signals;

i.e. compare signal 1 with signal 2, signal 3 with 4, and so on for a set number of signals;

This comparison can also be done across comparing multiple waveforms:

i.e. signal 1 is compared with signals 2, 3, 4 (and so on), then scan 2 is compared with signals 3, 4 (and so on), the process repeating for a set number of signals.

Alternative patterns are also possible

Techniques such as principle component analysis may be used to find these differences.

The results of these comparisons are combined via non-linear imaging, and produce the pixels to the resulting image, or sub-set of a larger image. The image can then be further enhanced and displayed in two or three dimensions by secondary means. Qualitative or quantitative details on the image can be obtained General Formulation The invention's overall algorithm combines multiple difference-based measurements in order to derive information about the blood flow. The algorithm involves the following steps:

Transmitting and receiving multiple signals through the medium containing the static and dynamic components. The position of the transmitter/receiver equipment of the imaging device 12 should remain fixed with respect to the static component of the medium.

Each A-Scan in the received data can be filtered to remove the background noise, and enhance the signal via Low-Pass, Band-Pass, or High-Pass Filters, Convolutions, or Cross Correlations with the known, or estimated signal from the scanning device any other variety of other denoising, and enhancing operations from those knowledgeable in the subject.

For each A-Scan the phase may be measured, as described below (see "Measuring Phase" subsection).

The differences are extracted using cross comparison of the waveforms as explained in the "General overview" subsection above. Information about the differences between the data may also be found by techniques such as principle component analysis.

Combine the above differences from all comparisons, corresponding to a specific instance or an interval of time, via summation/integration of their absolute values (possibly of a complex number), squared values; or using any other method that highlights the cumulative changes and suppresses the static component. Information from two separate difference calculations may be combined to produce a new result.

Use obtained number to assign a value to a pixel in the 2D or 3D image. The coordinates of said pixel correspond to spatial-temporal location of the medium where the wave incurred the phase changes measured above. The process above is repeated for different positions of the receiver, or different elements in the receiver, obtaining data at a new spatial position in the object. The formulation can be adjusted to the various receiver types (single element, 1D, and 2D discussed earlier) by those knowledgeable in the subject. The formulation can be adjusted for the different comparison methods discussed above by those knowledgeable in the subject. The formulation can be adjusted for continuous phase information by those knowledgeable in the subject.

Measuring the Phase

Phase information can be obtained via such methods as Fourier Transform (Short Fourier Transforms, Short Shifting Fourier Transforms, and other Fourier methods), and Hilbert Transform. The method need not be restricted to only these transforms. The phase of the signal can be measured at a particular instance of time, such as with a Hilbert transform; or over a finite interval of time, such as with short-Fourier transform. By comparing multiple phase measurements of the signal at various instances in time, or intervals of time, the method obtains information can be obtained about blood flow at various depths through the tissue (corresponding to the time interval). By collecting and processing a number of signals propagating at different spatial positions, it is possible to measure the phase and derive the blood flow information over the entire volume of said medium. From this a variety of 2D and 3D images of the blood flow in the medium can be obtained (3D structure, cross sections, box sections, etc.)

3. Further Processing

The receiver's position can be altered incrementally to increase the size of the image created. The receiver's position can be altered to enhance a previously imaged area, obtain a finer detailed image, or image the area again. Additional image processing techniques can be used to scale, enhance, smooth, or display the image. The image created can be further refined to deal with irregularities introduced by inhomogenoties in the skull, or tissue.

The present method uses a statistical, or multiple information approach to enhance information lost due to the presence of the skull, or other object.

Multiple signals are obtained (and processed to enhance the signal)

Each signal is compared mathematically to all other signals, this allows the process to turns N signals into roughly $N^2/2$ measurements Multiple comparisons are then combined.

The invention is not specifically probing the nonlinear properties of the medium, and as such the invention does not require physical change in signals transmitted into the medium. The invention assumes flowing liquids are flowing and dynamic (non-static), and that this flow of scatterers in the liquid produces different received signals due to this flow producing (a changing speckle response). It is this speckle property of the flowing liquid that is analyzed not nonlinear response.

Possible ways to enhance these speckles from the medium to enhance image contrast have been disclosed above.

The removal of phase inversion (pulse inversion) means the present method requires no specific pulse paring for the pulse comparison. The invention uses N like signals, and allows for the processed signal 1 to be compared to any processed signal from signal 2 through signal N by mathematical means (i.e. subtraction). This multi-comparison option further increases the contrast and detection of the flow.

Comparison of multiple signals by this invention removes static objects, and truly images the flowing region. Pulse inversion techniques assume a flow is essentially static, and there is no differentiation between static and dynamic regions. This method provides options to use, and enhance, A-Scan data (A-Scan data can then used to make 2D B-Scans, 3D C-Scan images, or the 2D and 3D flow images of this invention)

In accordance with the provisions of the patent statutes and jurisprudence, exemplary configurations described above are considered to represent a preferred embodiment of the invention. However, it should be noted that the invention can be practiced otherwise than as specifically illustrated and described without departing from its spirit or scope.

We claim:

1. A method for imaging a flowing media behind static regions including the steps of:
   a) obtaining a plurality of acoustic echo signals containing information about speckle properties of the flowing media;
   b) comparing each of the plurality of acoustic echo signals to each of the others of the plurality of acoustic echo signals; and
   c) removing the static regions from the plurality of acoustic echo signals during said step b).

2. The method of claim 1 wherein said step b) includes subtracting the plurality of acoustic echo signals from one another.

3. The method of claim 1 further including the step of enhancing the speckle properties of the plurality of acoustic echo signals by filters or other denoising operations.

4. The method of claim 1 further including the step of enhancing the speckle properties of the plurality of acoustic echo signals by convolution or correlation operations.

5. The method of claim 1 further including the step of enhancing the speckle properties of the plurality of acoustic echo signals by transmission to phase space.

6. The method of claim 5 wherein said step b) includes comparing the differences between the plurality of acoustic echo signals.

7. The method of claim 5 wherein said step b) includes comparing the plurality of acoustic echo signals via subtraction.

8. The method of claim 1 wherein the comparing in step b) is subtracting.

9. The method of claim 1 further including the step of:
   d) combining the results from each of the comparisons of step b).

10. The method of claim 1 wherein said step b) includes comparing each of the plurality of acoustic echo signals with each of the others of the plurality of acoustic echo signals via principle component analysis or cross comparison subtraction methods.

11. The method of claim 1 further including the step of combining the results from each of the comparisons of step b).

12. The method of claim 1 wherein the flowing media is blood within a skull and within soft tissue, wherein the static regions are the soft tissue within the skull.

13. The method of claim 1 wherein said step a) is performed at a location fixed relative to the static regions such that the plurality of acoustic echo signals pass through the same static regions.

14. The method of claim 1 wherein step a) is performed by a transmitter that remains fixed with respect to the static regions and generates a plurality of acoustic signals that result in the plurality of acoustic echo signals.

15. The method of claim 1 wherein step a) is performed by a transmitter that remains fixed with respect to the static regions and generates a plurality of acoustic signals that result in the plurality of acoustic echo signals.

16. A method for imaging a flowing media behind static regions including the steps of:
    a) obtaining a plurality of acoustic echo signals containing information about speckle properties of the flowing media;
    b) comparing the plurality of acoustic echo signals to one another; and
    c) removing the static regions from the plurality of acoustic echo signals during said step b),
wherein the flowing media is blood within a skull and within soft tissue, wherein the static regions are portions of the skull.

17. The method of claim 16 wherein the portions of the skull are of varying thickness.

18. The method of claim 16 wherein said step b) includes subtracting the plurality of acoustic echo signals from one another.

19. The method of claim 16 further including the step of enhancing the speckle properties of the plurality of acoustic echo signals by filters or other denoising operations.

20. The method of claim 16 further including the step of enhancing the speckle properties of the plurality of acoustic echo signals by convolution or correlation operations.

21. The method of claim 16 further including the step of enhancing the speckle properties of the plurality of acoustic echo signals by transmission to phase space.

22. The method of claim 21 wherein said step b) includes comparing the differences between the plurality of acoustic echo signals.

23. The method of claim 16 further including the step of:
    d) combining the results from each of the comparisons of step b).

24. A method for imaging a flowing media behind static regions including the steps of:
    a) obtaining a plurality of acoustic echo signals containing information about the speckle properties of the flowing media;
    b) enhancing the speckle properties of the plurality of acoustic echo signals by transmission to phase space;
    c) comparing the plurality of acoustic echo signals to one another; and
    d) removing the static regions from the plurality of acoustic echo signals during said step c),
wherein the transmission to phase space generates a plurality of phase signals and wherein said step b) includes comparing dissimilarities between the plurality of phase signals via principle component analysis or cross comparison subtraction.

25. The method of claim 24 wherein step a) is performed by a transmitter that remains fixed with respect to the static regions and generates a plurality of acoustic signals that result in the plurality of acoustic echo signals.

26. The method of claim 25 wherein the flowing media is blood within a skull and within soft tissue, wherein the static regions are the soft tissue within the skull.

27. A method for imaging blood flowing within a skull including the steps of:
    a) transmitting a plurality of signals toward a portion of the skull and the blood flowing behind the portion of the skull;
    b) receiving a plurality of echo signals from the portion of the skull and from the blood containing information about speckle properties of the flowing media;
    c) comparing the plurality of echo signals to one another; and
    d) based upon said step c), removing portions of the plurality of echo signals caused by the portion of the skull from the plurality of echo signals received during said step b).

28. The method of claim 27 wherein the portion of the skull includes areas of varying thickness.

29. The method of claim 27 wherein step a) is performed by a transmitter that remains fixed with respect to the skull and generates a plurality of acoustic signals that result in the plurality of acoustic echo signals.

* * * * *

UNITED STATES PATENT AND TRADEMARK OFFICE
CERTIFICATE OF CORRECTION

PATENT NO. : 9,613,401 B2
APPLICATION NO. : 13/863357
DATED : April 4, 2017
INVENTOR(S) : Roman Gr. Maev, Jeffrey T. Sadler and Eugene Malyarenko Page 1 of 1

It is certified that error appears in the above-identified patent and that said Letters Patent is hereby corrected as shown below:

In the Claims

In Claim 29, Column 8, Line 43; after "plurality of" delete "acoustic"

Signed and Sealed this
Seventeenth Day of October, 2017

Joseph Matal
*Performing the Functions and Duties of the*
*Under Secretary of Commerce for Intellectual Property and*
*Director of the United States Patent and Trademark Office*